(12) United States Patent
Kim et al.

(10) Patent No.: US 8,075,940 B2
(45) Date of Patent: Dec. 13, 2011

(54) BIOACTIVE MATERIAL COATING METHOD AND TUBE

(75) Inventors: Dae-Joong Kim, Seongnam-si (KR);
In-Su Baek, Anyang-si (KR);
Jong-Sang Park, Seoul (KR);
Hye-Yeong Nam, Cheongju-si (KR);
Chengzhe Bai, Goyang-si (KR)

(73) Assignees: Sungkyunkwan University Foundation for Corporate Collaboration, Gyeonggi-Do (KR); Samsung Life Welfare Foundation, Seoul (KR)

( * ) Notice: Subject to any disclaimer, the term of this patent is extended or adjusted under 35 U.S.C. 154(b) by 0 days.

(21) Appl. No.: 12/866,235

(22) PCT Filed: Jan. 19, 2009

(86) PCT No.: PCT/KR2009/000282
§ 371 (c)(1),
(2), (4) Date: Aug. 4, 2010

(87) PCT Pub. No.: WO2010/082698
PCT Pub. Date: Jul. 22, 2010

(65) Prior Publication Data
US 2011/0029069 A1 Feb. 3, 2011

(30) Foreign Application Priority Data
Jan. 15, 2009 (KR) .......................... 10-2009-0003472

(51) Int. Cl.
*A61L 33/00* (2006.01)

(52) U.S. Cl. ....... 427/2.25; 427/2.1; 427/2.24; 427/230; 427/430.1; 427/434.2

(58) Field of Classification Search ................. 623/1.13; 604/265; 607/120; 427/2.25
See application file for complete search history.

(56) References Cited

FOREIGN PATENT DOCUMENTS
KR 10-0596218 7/2006

OTHER PUBLICATIONS
International Search Report, mailing date Feb. 11, 2010, for corresponding International Application No. PCT/KR2009/000282.

*Primary Examiner* — Dah-Wei Yuan
*Assistant Examiner* — Andrew Bowman
(74) *Attorney, Agent, or Firm* — Intellectual Property Law Group LLP

(57) ABSTRACT

A method for coating bioactive material and a structured coated with a bioactive material are disclosed. The bioactive material coating method includes: flowing a coating solution, produced as a bioactive material is dissolved in a mixed solvent, inside a structure having a lumen; and coating the bioactive material on at least one of inner and outer surfaces of the structure, with different concentrations. The mixed solvent is mixed with two or more solvents having different features. The occurrence of the strangulation of blood vessels and inflammation can be reduced. An increase in the size of the myofibroblast is not suppressed. The coating solution is produced as a medication is dissolved in a mixed solvent, where the mixed solvent is produced as a polar solvent and a nonpolar solvent are mixed with each other at a certain ratio.

7 Claims, 1 Drawing Sheet

[FIG. 1]
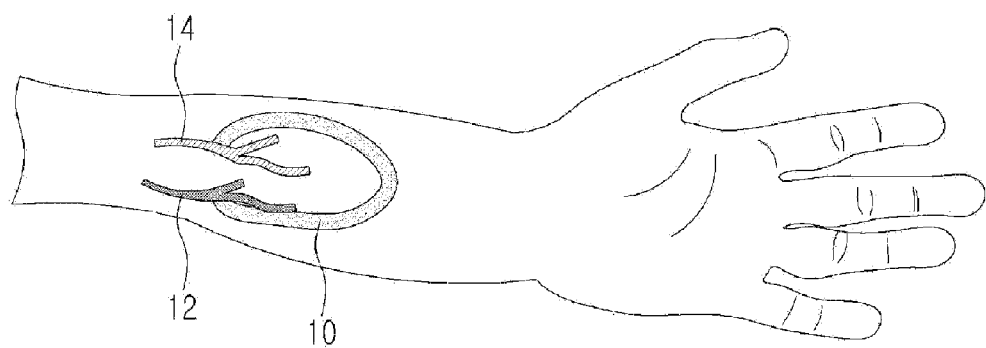
[FIG. 2]
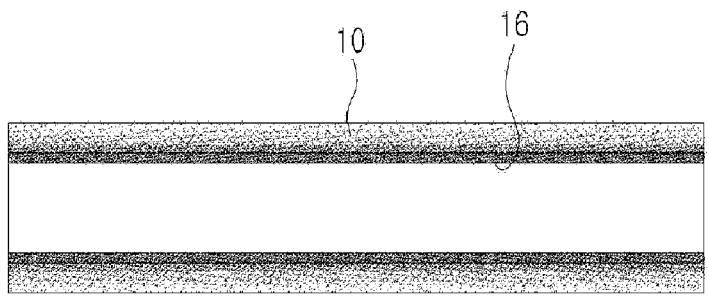

BIOACTIVE MATERIAL COATING METHOD AND TUBE

BACKGROUND OF THE INVENTION

1. Field of the Invention

The present invention relates to a method for coating bioactive material and a structured coated with a bioactive material.

2. Background of the Invention

Patients with renal insufficiency undergo hemodialysis therapy. In recent years, the number of renal insufficiency patients has increased. Most patients using hemodialysis therapy developed renal insufficiency due to glycosuria and hypertension. In that case, the patents are likely to also suffer from serious ateriosclerosis. In order to receive hemodialysis therapy, the flow of blood needs to be uninterrupted in the connection portion between the vein and artery for a long period of time.

In Korean Patent, Registration No. 10-0596218 entitled "ARTERIOVENOUS TUBE COATED WITH MEDICATION FOR HEMODIALYSIS PATENT," a tube was disclosed. That is, an artificial blood vessel of an expanded polytetrafluoroethylene (e-PTFE) is coated with a medication that suppresses the increase of cells and the generation of inflammation, thereby suppressing the strangulation of blood vessels and the inflammation that may be generated when it is planted in the vein and artery.

The e-PTFE is a thin film having fine pores. The e-PTFE is produced as PTFE is expanded in various directions by being extruded at a high temperature and a high pressure. Since the e-PTFE has a small frictional coefficient, it can delay the adsorption of protein when contacting the blood. That is, since the e-PTFE has an anti-thrombosis quality, it is used as a material for creating an artificial blood vessel.

As shown in FIG. 1, an artificial blood vessel connects an artery and a vein of a hemodialysis patient. In order to provide an internal arteriovenous fistula to a patient, a particular portion of the human body needs to be incised by a hypodermic portion and then the artery and vein are perforated. After that, the perforated artery and vein are connected to both ends of an artificial blood vessel. The connected artificial blood vessel is sutured in the incised portion and serves as a blood path to take hemodialysis, together with capillary connecting the arteries and the veins. During the hemodialysis, the artificial blood vessel is connected with an injector from a hemodialyzer, so that the hemodialyzer is located between the artery and the vein.

It is preferable that a patient uses his blood vessel as an artificial blood vessel. However, since his or her blood vessels may be diseased, it is difficult to use it as it is, so an artificial path is established between the artery and the vein. When the artificial blood vessel as the artificial path has been established, neointimal hyperplasia occurs in the portion of connection between the artery and the artificial blood vessel and between the vein and the artificial blood vessel. In that case, an edema forms at the connection portion or the blood vessels are strangulated, so that the artificial blood vessel cannot function as a path. Therefore, a new artificial blood vessel is needed to reduce the strangulation of blood vessels and the development of inflammation.

If the artificial blood vessel implanted to patients is tightly connected with its surrounding tissues, the patient can easily receive hemodialysis treatment. Otherwise, bleeding may occur at the site of the artificial blood vessel after hemodialysis treatment. Therefore, the implanted artificial blood vessel is required to be fixed to its surrounding tissues as the size of the myofibroblast increases.

On the other hand, although an artificial blood vessel, coated with paclitaxel used as an anticancer drug, can remarkably reduce the strangulation of blood vessels and the occurrence of inflammation, compared with an artificial blood vessel that is not coated with medication, it is still disadvantageous as it cannot suppress the increase of myofibroblast.

SUMMARY OF THE INVENTION

The present invention solves the above problems, and provides a method that coats medication on artificial blood vessels to suppress the occurrence of strangulation in the artificial blood vessels and in the anastomosis of arteries and veins, and the inflammation of surrounding tissues, allowing the myofibroblast to increase.

The present invention further provides artificial blood vessels coated with medication.

In accordance with an exemplary embodiment of the present invention, there is provided a bioactive material coating method including: flowing a coating solution, produced as a bioactive material is dissolved in a mixed solvent, inside a structure having a lumen; and coating the bioactive material on at least one of inner and outer surfaces of the structure, with different concentrations. The mixed solvent is mixed with two or more solvents having different features.

Preferably, the structure connects both ends to the circulation paths of a human body.

Preferably, the circulation paths of a human body are the blood vessels. The blood vessels are an artery and a vein used as a blood vessel approach path of a hemodialysis patient.

Preferably, one of the two or more solvents having different features is a polar solvent and another is a nonpolar solvent.

Preferably, the polar solvent is water and the nonpolar solvent is acetone.

Preferably, the bioactive material is a medication for suppressing neointimal hyperplasia. The bioactive material is a paclitaxel.

Preferably, the structure is a thin film of extended polytetrafluoroethylene (e-PTFE) having fine pores.

In accordance with another exemplary embodiment of the present invention, there is provided a tube, wherein a bioactive material is coated on at least one of inner and outer surfaces of a structure having a lumen, with different concentrations, in which the structure connects both ends to the circulation paths of a human body.

Preferably, the circulation paths of a human body are the blood vessels. The blood vessels are an artery and a vein used as a blood vessel approach path of a hemodialysis patient.

Preferably, the bioactive material is a medication for suppressing neointimal hyperplasia. The bioactive material is a paclitaxel.

Preferably, the structure is a thin film of extended polytetrafluoroethylene (e-PTFE) having fine pores.

As described above, the medication coating method, according to the present invention, coats medication on only the inner surface, contacting the blood, of the arteriovenous tube serving as an artificial blood vessel, thereby suppressing the occurrence of strangulation in blood vessels, inflammation, and thrombus, and the generation of new blood vessels. In particular, the increase of the myofibroblast is not suppressed outside the tube because the medication is not coated on the outer surface of the tube, which does not contact the blood.

BRIEF DESCRIPTION OF DRAWINGS

The features and advantages of the present invention will become more apparent from the following detailed description in conjunction with the accompanying drawings, in which FIG. 1 is a view where an arteriovenous tube connects an artery and a vein of a hemodialysis patient; and FIG. 2 is a cross sectional view illustrating an arteriovenous tube, whose inner surface is coated with medication according to an embodiment of the present invention.

BRIEF DESCRIPTION OF THE SYMBOLS IN THE DRAWINGS

10: arteriovenous tube
12: artery
14: vein
16: medication layer

DETAILED DESCRIPTION OF THE DRAWINGS

Hereinafter, exemplary embodiments of the present invention are described in detail with reference to the accompanying drawings. Detailed descriptions of well-known functions and structures incorporated herein may be omitted to avoid obscuring the subject matter of the present invention.

The present invention provides a method for coating a bioactive material on a structure having a lumen. In the following description, an embodiment of the present invention is explained based on a structure having a lumen, where the structure connects the artery and the vein to serve as a blood vessel approach path.

A lumen is the inner space of a tubular structure, such as an artery or intestine. In the following description of the present invention, a structure with a lumen will be generally referred to as a tube.

The structure with a lumen, i.e., a tube, is used to connect arteries and veins of a hemodialysis patient as shown in FIG. 1. In that case, the strangulation of blood vessels or the inflammation may occur around the arteriovenous tube. In order to increase the size of a myofibroblast around the arteriovenous tube and thereby to tightly connect the arteriovenous tube to the artery and the vein as well as to reduce the strangulation of blood vessels and the inflammation, medication, a bioactive material, needs to be coated on only the inner wall of the arteriovenous tube.

The medication serves to suppress neointimal hyperplasia or thrombosis in the blood vessel. That is, since the inside of the arteriovenous tube directly contacts the blood, it needs to be coated with the medication. On the contrary, the medication is not coated on the outside of the arteriovenous tube to help increase the size of a myofibroblast. When the medication is dissolved in a polar solvent and then the solution flows through an arteriovenous tube, the medication is only coated with only the inner wall of the arteriovenous tube. Since the arteriovenous tube is made of an extended polytetrafluoroethylene (e-PTFE), it allows for the permeation of a nonpolar solvent, such as an acetone, but not a polar solvent, such as water.

In order to uniformly dissolve the medication without precipitation, it needs to be dissolved in a nonpolar solvent, such as an acetone. In particular, in order to prevent oozing of the solvent where the medication dissolves out of the arteriovenous tube, the polarity of the solvent is raised using a polar solvent. That is, a coating solution is made in such a way that a polar solvent and a nonpolar solvent are mixed with each other at a certain ratio to make a mixed solvent having a proper polarity and then the medication is dissolved in the mixed solvent.

When the coating solution in which the medication is dissolved flows through the inside of the arteriovenous tube, it soaks into the arteriovenous tube so that the medication coats the inner wall of the arteriovenous tube.

Although the embodiment of the present invention uses an acetone as a nonpolar solvent, it should be understood, however, that the present invention is not limited to the embodiment. For example, it will be appreciated that the solvents may also use diethyl ether, ethyl acetate, dichloromethane, n-hexane, and chloroform, according to the solubility of medication. When the coating solution dissolving the medication soaks into the inside of the arteriovenous tube, the acetone is easily volatized, so that the medication can only coat the inner wall of the arteriovenous tube. That is, it is preferable that the nonpolar solvent employs a solvent, such as an acetone, which has a high volatility and can easily dissolve the medication.

It is preferable that the arteriovenous tube is made of an e-PTFE. The e-PTFE is an elastic fiber material. When the coating solution flows through the arteriovenous tube, it can easily soak into the arteriovenous tube if the ratio of the nonpolar solvent is higher than the ratio of the polar solvent. However, if the ratio of the nonpolar solvent is much higher than the ratio of the polar solvent, the coating solution may ooze out through the fine pores of the arteriovenous tube. Therefore, it is important to adjust the polarity during the preparation of the coating solution.

It is preferable that the polar solvent is water, the nonpolar solvent is an acetone, and the medication is paclitaxel used as an anticancer drug. It is also preferable that the ratio of the acetone to water is 9:1, 8:2 or 7:3. If the ratio of water is much lower than the ratio of acetone, the coating solution is almost nonpolar. In that case, the coating solution may deeply permeate into the inner wall of the arteriovenous tube, so that a relatively large amount of medication coats the inside of the arteriovenous tube. On the contrary, if the ratio of water is much higher than the ratio of acetone, the coating solution has a high polarity. In that case, the coating solution may slightly permeate into the inner wall of the arteriovenous tube, so that a relatively small amount of medication coats the inside of the arteriovenous tube.

Although the embodiment of the present invention employs paclitaxel as a medication, it should be understood, however, that the present invention is not limited to the embodiment. The present invention may use any mediation provided that they can suppress the strangulation of blood vessels or the occurrence of inflammation, for example, rapamycin, taclorimus, cyclosporine A, etc.

As described above, since the e-PTFE is made of a fiber material, it may be expanded according to the pressure of the coating solution flowing through the arteriovenous tube. If the pressure of the coating solution is too high, the coating solution may ooze out through the fine pores of the arteriovenous tube. Therefore, the pressure of the coating solution needs to be properly controlled in the arteriovenous tube. It is preferable to use a peristaltic pump so that the coating solution flows through the arteriovenous tube at a proper pressure. The peristaltic pump can control the flow speed and flow time of the coating solution.

Since the flow speed and flow time of the coating solution can be controlled, the concentration of the medication to be coated on the inside of the arteriovenous tube can also be controlled. The slower the flow speed of the coating solution and the longer the flow time of the coating solution, the higher the concentration of the medication to be coated on the inside of the arteriovenous tube.

As described above, when the coating solution containing the dissolved medication flows through the arteriovenous tube using the peristaltic pump, the medication slowly starts to permeate from the inner wall surface toward the outside of the arteriovenous tube. Therefore, as shown in FIG. 2, when the concentration of the coated medication on the inner side of the tube is thicker, the concentration of the coated medication on the outside of the tube is thinner. Since the medication is mainly coated on the inner part of the arteriovenous tube but rarely on the outer part, the size of the myofibroblast increases, reducing the strangulation in the portion around the arteriovenous anastomosis or the occurrence of the inflammation in the tissues around the arteriovenous tube. Therefore, the arteriovenous tube according to the present invention does not suppress the increase of the myofibroblast and is tightly fixed to its surrounding tissues.

Although the arteriovenous tube according to an embodiment of the present invention has explained based on the use for the hemodialysis patients, it should be understood that it can used as an artificial blood vessel for connecting arteries and veins and also be connected to lymphatic vessels.

The is, the arteriovenous tube according to the present invention can be used as an artificial blood vessel connecting the blood vessels or an artificial lymphatic vessel connecting lymphatic vessels. For example, the arteriovenous tube can be used for diseases, such as Critical Limb Ischemia. It can also be used as a replacement blood vessel, such as Coronary Artery Bypass Graft (CABG), as well as a blood vessel approach path.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The present invention can be widely applied to the medical technology sector.

What is claimed is:

1. A bioactive material coating method comprising:
   flowing a coating solution, produced as a bioactive material dissolved in a mixed solvent, inside a structure having a lumen; and
   coating the bioactive material on the structure to form a concentration of the bioactive material across a thickness of the structure that decreases from an inner surface of the structure to an outer surface of the structure,
   wherein the mixed solvent is made as a mixture of two or more solvents which permeate the structure to different extents.

2. The method according to claim 1, wherein the structure has two ends, and each end connects to a circulation paths of a human body.

3. The method according to claim 2, wherein:
   the circulation paths of a human body are blood vessels; and
   the blood vessels are an artery and a vein, wherein the structure serves as an access route to a blood vessel of a hemodialysis patient.

4. The method according to claim 1, wherein the two or more solvents are a combination of a polar solvent and a nonpolar solvent.

5. The method according to claim 1, wherein the bioactive material is a medication for suppressing neointimal hyperplasia.

6. The method according to claim 1, wherein the bioactive material is a paclitaxel.

7. The method according to claim 1, wherein the structure is formed of expanded polytetrafluoroethylene (e-PTFE) having fine pores.

\* \* \* \* \*